United States Patent [19]
Cohen

[11] Patent Number: 6,036,494
[45] Date of Patent: Mar. 14, 2000

[54] METHOD FOR COSMETICALLY IMPROVING AND ALTERING THE APPEARANCE OF TEETH

[76] Inventor: Morton Cohen, 647 Meadowbrook Dr., Huntingdon Valley, Pa. 19006

[21] Appl. No.: 09/054,898

[22] Filed: Apr. 3, 1998

[51] Int. Cl.[7] ..................................................... A61C 5/00
[52] U.S. Cl. ........................................ 433/217.1; 433/215
[58] Field of Search ............................. 433/217.1, 203.1, 433/222.1, 228.1, 215

[56] References Cited

U.S. PATENT DOCUMENTS

| | | | |
|---|---|---|---|
| 3,932,938 | 1/1976 | Mackta | 433/203.1 |
| 4,032,627 | 6/1977 | Suchan et al. | 424/54 |
| 4,097,994 | 7/1978 | Reaville et al. | 427/54 |
| 4,141,144 | 2/1979 | Lustgarten | 433/217.1 |
| 4,259,069 | 3/1981 | Lustig | 433/144 |
| 4,433,959 | 2/1984 | Faunce | 433/222.1 |
| 4,473,353 | 9/1984 | Greggs | 433/215 |
| 4,496,322 | 1/1985 | Sandham et al. | 433/217.1 |
| 4,512,743 | 4/1985 | Santucci et al. | 433/217 |
| 4,682,950 | 7/1987 | Dragan | 433/90 |
| 4,822,279 | 4/1989 | Greggs | 433/202.1 |
| 4,992,049 | 2/1991 | Weissman | 433/215 |
| 5,304,585 | 4/1994 | Bunker | 523/116 |
| 5,326,264 | 7/1994 | Al Kasem | 433/224 |
| 5,364,267 | 11/1994 | Fischer | 433/26 |
| 5,433,941 | 7/1995 | Patel | 433/217.1 |
| 5,512,611 | 4/1996 | Mitra | 433/228.1 |
| 5,565,152 | 10/1996 | Oden et al. | 264/19 |
| 5,593,303 | 1/1997 | Cohen et al. | 433/9 |
| 5,814,682 | 9/1998 | Rusin et al. | 433/228.1 |

OTHER PUBLICATIONS

Silverman E, Cohen M, Demke RS, Silverman M. A new light–cured glass ionomer cement that bonds brackets to teeth without etching in the presence of saliva. Am. JOrthod-DentofacOrthop1995;108:231–6.

Komori A, Ishikawa H. Evaluation of a resin–reinforced glass ionomer cement for use as an ortho–dontic bonding agent. Angle Orthod 1997; 67(3):189.

GC Fuji I. An improved glass ionomer luting cement. Brochure distributed by GC International Corp.

Bisco Aelite Seal Dual–cured pit and fissure sealant. Directions for use and material safety data sheet. Brochure distributed by Bisco, Inc., Itasca, IL 60143, Mar. 1996.

Komori A, Ishikawa H. Evaluation of a resin–reinforced glass ionomer cement for use as an orthodontic bonding agent. The Angle Orthodontist 1997; 67(3):189–95.

Bayne SC, Thompson JY, Swift Jr. EJ, Stamatiades P, Wilkerson M. A characterization of first–generation flowable composites. JADA 1998; 129:567–79.

Silverman E and Cohen M. Bonding of orthodontic attachments using ultraviolet light polymerized adhesives. In Buonocore MG (Ed.), The Use of Adhesives in Dentistry. Charles C. Thomas, Publisher. Springfield, IL, 1975:372–88.

*Primary Examiner*—John J. Wilson
*Attorney, Agent, or Firm*—Paul & Paul

[57] ABSTRACT

A method for altering the appearance of teeth, including whitening or otherwise colorizing teeth, to cover discolorations and stains, or to provide a fashionable color on the tooth which can be selectively removed, the method including selecting the color to be applied, preparing the colorized compound to be applied to a tooth, exposing the tooth to be covered, applying a colorized compound to the enamel surface of the tooth, and allowing the compound to dry on the tooth, and selectively removing the compound from the tooth.

29 Claims, 1 Drawing Sheet

METHOD FOR COSMETICALLY IMPROVING AND ALTERING THE APPEARANCE OF TEETH

BACKGROUND OF THE INVENTION

1. Field of the Invention

The present invention relates to the field of cosmetically improving and altering the appearance of teeth.

2. Brief Description of the Prior Art

Many procedures are done to improve the appearance of teeth. Teeth are filled to replace dentin invaded by bacteria, and can be capped to replicate a removed or abraded portion of a tooth.

The teeth of individuals widely vary in their appearance and shape. This is due to the genetic make-up of the individual, but can also be affected by age, and the degree of contact with various foods and medications, both those superficially contacting the teeth and from the internal effects of the medication. The teeth of some individuals exhibit a yellow appearance while those of others may be whiter. While aging is often considered a "natural" cause of tooth discoloration, other factors commonly attributed to tooth discoloration can include chemical exposure to tannins, which are found in red wines, and brewed beverages such as coffees and teas. Additional discoloring chemicals include those not naturally occurring in foods, but rather, manufactured or synthesized compounds, such as, for example, the compounds found in medications, like antibiotics, including tetracycline and other pharmaceuticals. The common practice of using doses of tetracycline to cure facial, acne blemishes has been known to contribute to the discoloration of teeth. Aside from these chemicals, even excess brushing has been can create discoloration by repeated contact with fluoride compounds commonly present in most toothpastes.

Many have attempted to confront the problem of tooth discoloration by proposing various solutions to whiten the teeth. One such method of tooth whitening involves the bonding of veneers onto the buccal or labial surfaces of a tooth. The veneer is usually constructed and applied by a dentist using dental bonding techniques to attach it to the tooth. Various veneers have been described in several U.S. Pat. No., see, e.g. 4,992,049 "Method for Applying a Veneer Facing to a Tooth"; U.S. Pat. No. 4,822,279 "Article for Cosmetic Restoration of Anterior Teeth" (which uses a glazed porcelain labial veneer); U.S. Pat. No. 4,682,950 "Device and Method of Bonding and Veneering Dental Material to a Tooth" (syringing composite material to a tooth surface which has been etched and coated with a bonding material); U.S. Pat. No. 4,473,353 "Method for Cosmetic Restoration of Anterior Teeth" (wherein a glazed porcelain veneer is bonded to a patient's tooth); and U.S. Pat. No. 4,433,959 "Composite Laminate Dental Veneer Containing Color Systems" (a veneer which is molded and then attached to the labial enamel surfaces of teeth).

Other attempts to whiten teeth are also known to include bleaching the teeth. Often the bleach is applied in the form of hydrogen peroxide, which can be obtained in drug stores by consumers. Because of the delicacy of applying hydrogen peroxide in one's mouth, some dentists carry out the procedure in their offices, using a stronger peroxide than can be purchased by the consumer. There are even pastes, sold over the counter, to the consumers which claim to whiten teeth. Often ordinary toothpastes make this claim, but increasingly appearing in the marketplace for purchase by consumers are pastes with the chemical compound sodium bicarbonate (baking soda), which may also contain peroxide. While chemical bleaching of teeth has been done to provide whiter-looking teeth, with its use there exists danger to the enamel of the teeth, especially if excessive exposure to chemical bleaches occurs. Further, chemical bleaching is understood in many cases to require multiple applications, and, hence, repeated use of the chemical. Even when applied by a dentist, precautions may be taken to prevent peroxide solution from contacting the patient's gums, which if otherwise allowed to come into contact therewith can be painful and cause damage to the gums. In cases of certain stains, bleaching may not be effective, and the stain may remain.

There are even procedures involving abrasion of the tooth enamel to present a smooth surface which is lighter in appearance than the stained surface removed. This has limitations as to the number of times it can be done.

Furthermore, abrading or bleaching teeth can have deleterious side effects, including, increased sensitivity of the treated tooth to temperature, i.e. especially when hot and cold foods and drinks are consumed. This effect may subside within time, but often the need to repeat bleaching procedures regularly, gives rise to a period of time within which the treated tooth can be hypersensitive.

There are some prior art whitening methods which require etching steps that are carried out with phosphoric acids. The use of phosphoric acid is generally done by a dentist under controlled conditions, for example, in the dentist's office. Caustic acid etchants have been recognized to be corrosive to the soft tissues of the mouth. For example, orthophosphoric acid, in some venues, must be transported pursuant to specified requirements and restrictions. In addition, the long term physiological effects of acid etching, which are generally unknown, have led practitioners to question certain acid etching uses in the field of dentistry. See e.g. M. G. Buonocore, "The Challenge of Bonding to Dentin", The Acid Etch Technique, L. M. Silverstone and I. L. Dogon, Eds., Proceedings of the International Symposium at St. Moritz, Switzerland, Dec. 16–18, 1974, North Central Publishing Co. (St. Paul, 1975). See also, U.S. Pat. No. 5,304,585, which raises these concerns, the complete disclosure of which is herein incorporated by reference; and see Akira Komori, and Haruo Ishikawa, "Evaluation of a Resin-Reinforced Glass Ionomer Cement for Use as an Orthodontic Bonding Agent," The Angle Orthodontist, Vol. 67 No. 3, 1997, the complete disclosure of which is herein incorporated by reference. Further attempts to whiten teeth are disclosed in U.S. Pat. Nos. 4,032,627 "Tooth Whitening Cosmetic Composition"; U.S. Pat. No. 4,097,994 "Dental Restorative Composition Containing Oligomeric Bis-GMA Resin and Michier's Ketone"; U.S. Pat. No. 4,141,144 "Dental Material and Method For Controlling Tooth Lustre"; and U.S. Pat. No. 4,512,743 "Method for Masking Discoloration on Teeth." U.S. Pat. Nos. 4,512,743 and 4,141,144, each use phosphoric acid application to the tooth in their treatments. U.S. Pat. No. 4,097,994 discloses a photocurable compound, which is used with a specific ultraviolet sensitizer and a peroxide catalyst to cure the compound. Furthermore, phosphoric acid etching generally disposes grooves in the tooth enamel in the nature of about 50 to 60 μm. This order of etching is visible and is noticed in the form of a dull tooth surface.

U.S. Pat. No. 4,032,627, referenced above, discloses the use of an alcohol-soluble composition to be applied to the surface of a tooth to whiten the tooth's appearance. This composition is suggested to be applied by the user. However, although this disclosure attempts to provide an extended wearing time for its compound, the composition is readily worn off by the abrasive action of food eaten after the compound is applied to the teeth, with certain, more abrasive, harder, foods causing faster wear of the composition from the tooth than other, softer, foods.

A need exists for a temporary tooth whitening system which can be safely applied by the wearer, or without the need for specially trained dental personnel. The tooth whitening to be achieved should also have stability and be able to resist removal or solvation by foods and beverages, but should be able to be removed whenever the user desires.

SUMMARY OF THE INVENTION

A novel method for altering the appearance of teeth is provided by the present invention, where an individual, in his or her own home, or in a beauty parlor, or other non-medical office, can apply a colorized compound to his or her teeth to cosmetically alter and/or improve the appearance of the teeth. The present method can be used to whiten anterior teeth, and can even be done in the presence of existing saliva which may be present on the tooth. The method provides a removable coating which can comprise a colorized coating which can be removed and replaced with other colorized coatings or no coatings at the user's discretion. Expensive or dangerous drying apparatus are not required. Further, the present invention can be applied with or without an etching step, thereby avoiding the hazards inherent to use of caustic acid etchants, such as phosphoric and phosphonic acids. Moreover, when an individual's teeth, in accordance with the present method, require pre-treatment prior to application of the covering compound, the application of a naturally occurring substance can be used to facilitate adhesion. The substance can be lemon juice or lime juice, which unlike caustic acids, contains citric acid, which can be purchased by the consumer user of the compound which is to be applied by the present method. In an alternate embodiment of the invention, polyacrylic acid is applied to the tooth surface prior to contact with the covering compound.

The present invention also provides a novel method for temporarily changing the color of a tooth. A palette system is provided wherein a user or wearer can select a color from one, or a combination of one or more, colorizing compounds. The selected or created color can then be incorporated with the other steps of the present method to provide a unique appearance to a tooth. The present method permits the user to mix his or her own colors or to select a color from one or more prepared provided colors.

It is an object of the present invention to provide a novel method for improving the appearance of teeth.

It is a further object of the present invention to accomplish the above object by whitening the teeth to improve their appearance.

It is a further object of the present invention to improve the appearance of teeth by covering stains or discolorations on a tooth by matching a colorized compound to an individual's teeth and applying the colorized compound on the surface of said stained or discolored teeth.

A further object of the present method is to improve the appearance of a tooth by applying a colored or shaded composition to the tooth.

A further object of the present invention is to coordinate colors of a tooth with other health and beauty aids by applying a method for colorizing a compound and applying it to a tooth.

Another object of the present invention is to provide a method for applying a compound to a tooth which can remain on the tooth during eating and other activity, and can be removed at the wearer's discretion, to leave the tooth as it appeared before the application of the compound.

A further object of the present invention is to provide a novel method of improving the appearance of a tooth which includes applying a compound to the tooth and removing the compound from the tooth with a pick.

A further object of the present invention is to provide a method for improving the appearance of a tooth which can be repeated by the wearer, to change the appearance of a tooth, on a regular basis if the wearer desires, without having damaging effects on the tooth enamel.

Another object of the present invention is to provide a method which includes a color matching system wherein the user mixes components to colorize the composition to be applied to the tooth to the desired hue or color, which can be a tooth color or a non-tooth color.

It is another object of the present invention to accomplish the above objects by repeating application and removal of the compound on a tooth for different colors as the user determines and selects.

BRIEF DESCRIPTION OF THE DRAWING FIGURE

FIG. 1 is a flow chart illustrating an embodiment of the present method corresponding to example 3 below.

DETAILED DESCRIPTION OF THE INVENTION

Figure 1:
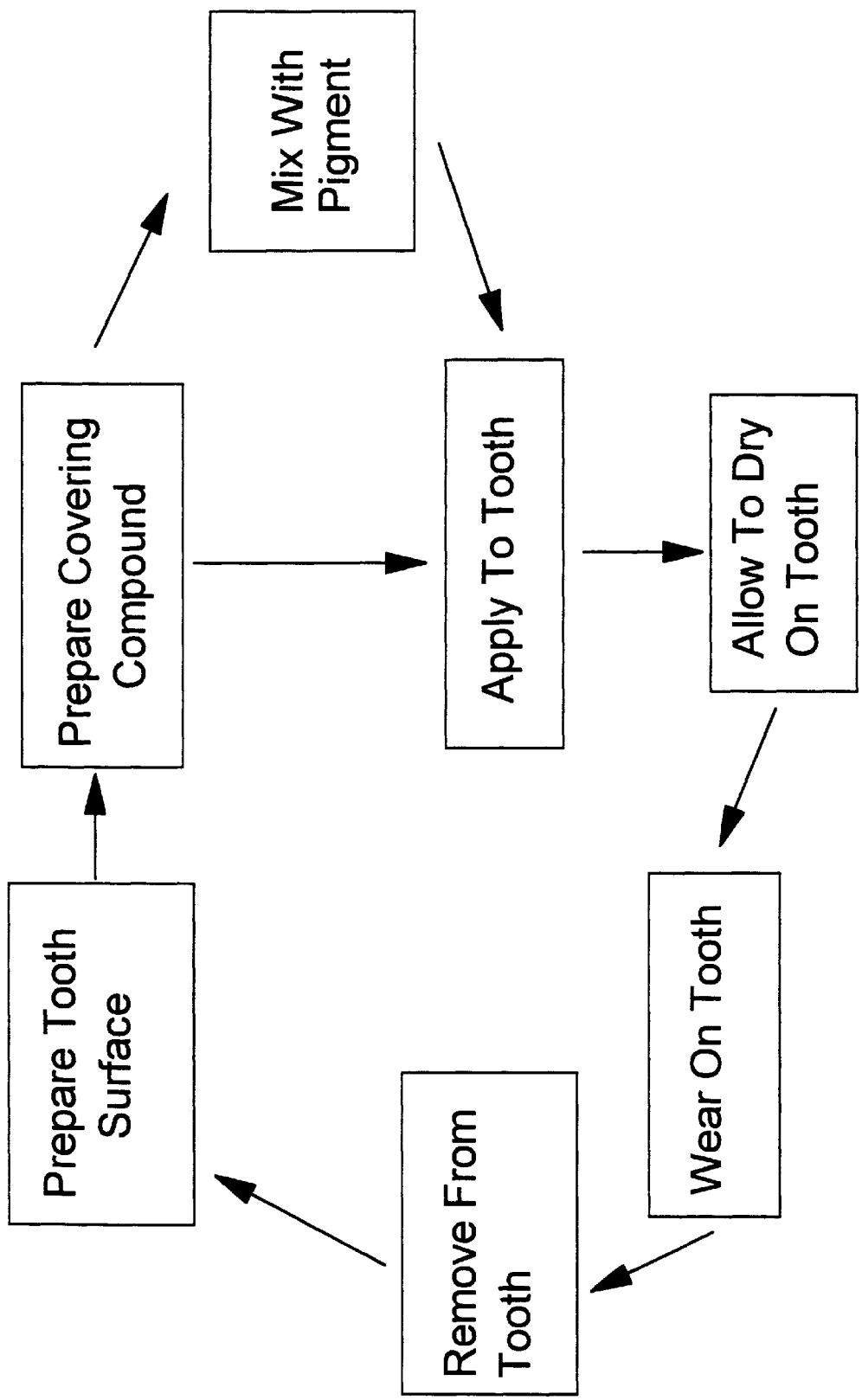

The present invention provides a method for altering the appearance of teeth. The altered appearance can be the removal of stains or discoloration caused by disease, chemical exposure or aging. Generally the enamel of teeth is bound to tannins and other chemicals which remain on the enamel, in the form of a stain, which cannot be removed by brushing. When bacteria invade a tooth, generally, the dentin is eroded and a filler inserted to take the place of the lost portion of the tooth. Amalgams containing mercury are commonly used for filling teeth.

The present method provides for the application of a Bis-GMA or glass ionomeric compound to the surface of a tooth to cover discolorings which are present on the tooth. The covering compound to be applied by the present method comprises an opaque material which masks the tooth surface. One example of a compound used in accordance with the present method, is a Bis-GMA compound manufactured by Bisco, Inc., of Itasca, Ill., under the name AELITE-SEAL™ Pit and Fissure Sealant. This material is sold for filling posterior teeth and specifically for filling fissures in the teeth. Since the posterior teeth are not generally visible in a person's smile or when talking, the filling use of the Bis-GMA compound is appropriate. However, the use of a modified Bis-GMA sealant compound is employed in the present method in accordance with and as defined by the present steps for its application.

Another material which can be used in the present invention is a glass ionomer. A glass ionomer composition is disclosed in U.S Pat. No. 5,593,303 "Attachment of Orthodontic Brackets," the complete disclosure of which is herein incorporated by reference. The uses of glass ionomers heretofore have been associated with dental adhesives. The glass ionomers described in the '303 patent are used with a wet surface as an adhesive for bonding orthodontic fixtures to a tooth. The present method can employ a glass ionomer compound, and more preferably one which contains finely divided particles of about 0.02 μm or less. The particles can comprise a fluoroaluminosilicate glass powdered compound. In addition, the components comprising the glass ionomer compound will preferably be compatible to provide a refractive index of the glass ionomer compound which will exhibit a lustre. Another glass ionomeric compound which can be used in accordance with the present invention is described in U.S. Pat. No. 5,063,257, the complete disclosure of which is herein incorporated by reference.

The covering compound is applied to the teeth in the present invention by painting it onto the tooth surface, preferably with a brush. This enables the composition to be evenly distributed to cover the entire tooth, and furthermore, without an excessive buildup or absence of material in one spot of the tooth. Alternately an aerosol suspension can be used to apply the covering compound to the tooth. For example, a small tube can be used through which the aerosol can be propelled for application onto the tooth. This facilitates even distribution of the covering compound on the tooth surface and avoidance of coverage on gums, skin and other non-tooth surfaces.

The present method also provides palette means for controlling the colorizing of the tooth. The palette means preferably comprises a plurality of pigments which are present in individual quantities for adding to the covering composition to be applied to the tooth. The palette means preferably is provided with a plurality of pigment means which contain tooth-colored pigments which can be matched to the individual user's tooth color. In addition, the palette means can contain colorful shades, such as, for example, blue, pink, pastel colors, or any other color which is supplied in the form of a pigment compound which can be mixed with the base covering compound and then be applied to the tooth by painting on the tooth.

The method can be carried out, for example, by providing a tray having a series of compartments containing tooth-colored pigments arranged in one row and a series of colorizing pigments in other rows. A larger compartment can be provided for the base compound or components. The compartments can have resealable covers which can be opened and closed by the user to remove a pigment or compound as needed. A mixing area can also be provided and can also have a cover.

In some circumstances, it may be desirable to etch a tooth surface to provide microscopic pits for facilitating adhesion of a compound to be applied thereto. Etching provides an increased surface area of the tooth. However, the present method also requires removability of the temporary tooth coating. In a preferred embodiment of the invention, the teeth of an individual can be pretreated with citric acid, of the same weakness of that concentration contained in lemon juice. This facilitates the colorized composition to be retained on the tooth's surface, such as, for example, when a Bis-GMA type base compound is used. The citric acid prepares the surface of the tooth to receive the compound which is to be painted on the tooth. The method contemplates application of the tooth enhancing composition by an individual user or wearer having no special training or knowledge in dentistry. In this case, lemon juice can be used, since it will be easily obtained by the user. Alternately, citric acid solutions can be prepared or provided having the same general concentration as citric acid in lemon juice. By the use of the etching step, very small grooves or pits are formed on the tooth surface, which are approximately 5 to 10 μm or less. This enables the wearer of the compound to restore a treated tooth to its original appearance when desired by removing the covering compound. Another acid used in an alternate embodiment of the present invention is polyacrylic acid.

The covering compound, for example, can be prepared by taking a Bis-GMA type base material and providing an amount of a pigment which becomes the base pigment. To this pigmented base compound, the user can customize the color with the colorizing means, by selecting and combining pigment items and admixing the selected pigment items with the base compound. In addition, other elements, such as reflective means can be admixed as well to provide additional unique alteration of the tooth. For example, polymer particles, such as glitter, can be added to provide a sparkle effect to the tooth. In the case of the Bis-GMA compound, it may be prepared by premixing Bis-GMA with a suitable activator or catalyst, which can, for example, comprise a peroxide compound, such as benzoyl peroxide, and adding one or more pigments. The base compound to which colorizers can be added can include a Bis-GMA compound which is pigmented with titanium dioxide or other suitable pigment compounds. Since Bis-GMA itself (2,2-bis[4-(3-methacryloxy-2-hydroxypropoxy)-phenyl]-propane) is generally a transparent compound, it will preferably be made opaque for use as a base compound in the present method.

In the case of an alternate embodiment wherein a glass ionomer is used, the tooth surface preferably will be wet. The glass ionomer can be used as the base compound to which further pigments and colorizers can be admixed prior to application on the tooth. Preferably, the etching step will not be required when using the glass ionomer compound. However, where it is advantageous to use an etching step, the etching will be consistent with that described above, wherein pits, in the order of about 5 to 10 μm in depth, or preferably even less, are formed. For example, the glass ionomeric compound can comprise a liquid component and a powder component which are mixed together to form a base compound which can be colorized. The powdered component can, for example, comprise the fluoroaluminosilicate glass powder. It is particularly preferred to have particle sizes in the range of about less than 0.02 μm. The remaining component comprising the glass ionomeric cement can be comprised of a liquid including a carboxylic acid polymer, a polymerizable unsaturated organic compound containing at least one $CH_2=C(R1)—COO—$ group, wherein R1=H or $CH_3$, a polymerization catalyst, water, a surface active agent, and a reducing agent.

A colorizing pigment can be supplied in the form of a modified food starch or other color additive. The pigment can be supplied with the fluroaluminosilicate powder, or can be provided in solution with the liquid components. In addition, the glass ionomeric material can be supplied to the user with a tooth-colored shade, and can be further mixed for colorization by the user.

The colorizing means of the present invention preferably can comprise a color additive, such as, for example, a dye, pigment or substance that can impart color when added or applied to substance. Those particularly preferred include color additives of the type commonly used with a food, drug, cosmetic or in connection with the human body, especially color additives permitted for use in foods which are classified as "certifiable" or "exempt from certification." For example, the colorizing compound employed with the present method can include the exempt pigments, such as, for example, those listed below, derived from natural sources such as vegetables, minerals or animals, and man-made counterparts of natural derivatives. In addition, FDA certified pigments, such as, for example, the nine additives listed below can also be used.

Certified Color Additives

FD&C Blue No. 1 (Dye and Lake)
FD&C Blue No. 2 (Dye and Lake)

FD&C Green No. 3(Dye and Lake)
FD&C Red No. 3 (Dye)
FD&C Red No. 40 (Dye and Lake)
FD&C Yellow No. 5 (Dye and Lake)
FD&C Yellow No. 6 (Dye and Lake)
Orange B
Citrus Red No. 2

Colors Exempt from Certification

Annatto extract
B-Apo-8'-carotenal
Beta-carotene
Beet powder
Canthaxanthin
Caramel color
Carrot oil
Cochineal extract (carmine)
Cottonseed flour, toasted partially defatted, cooked
Ferrous gluconate
Fruit juice
Grape color extract
Grape skin extract (enocianina)
Paprika
Paprika oleoresin
Riboflavin
Saffron
Titanium dioxide
Turmeric
Turmeric oleoresin
Vegetable juice The form of the additive for use in the present invention preferably includes dye form additives, but may also include lake forms which are compatible with the base covering composition. Water soluble dyes, provided in the form of powders, granules, liquids or other special-purpose forms can be used in accordance with the present method. Lakes, the water insoluble form of the dye, are generally used for coloring products which do not contain adequate moisture to dissolve the dyes. For example, if a suspension of color is to be used, a lake form additive can be employed. The color additive provided in the form of a lake may, for example, be used with other tooth appearance enhancing means such as glitter particles.

The present method includes the step of painting the compound on a tooth which is in its in vivo environment and an intermediary is not required. The naturally occurring saliva may be present on the tooth, and the compound can be applied with the saliva being present. Alternately, the method can include applying the compound to a tooth by spraying. For example, a compressed gas propellant, such as an aerosol, can be utilized to provide delivery of the covering compound to the tooth.

The selected compound is painted on the tooth and permitted to harden. The hardening of the compound occurs within about two to three minutes. A shell-is then formed by the compound over the tooth surface on which it was applied and becomes attached to the tooth. The tooth thereby exhibits a new appearance, attributable to the compound.

The compound exhibits permanence and withstands normal buccal functions such as, for example, brushing, eating, chewing, contacting foods and beverages, and other functions carried out with one's teeth. The method applies a covering on the tooth which maintains a uniform appearance and is further resistant to staining. In addition, the covering protects the tooth against further staining and contact with bacteria and chemicals. The method applies a thin coating to the tooth which does not interrupt the user's normal mouth functions, and does not feel uncomfortable to a user.

The method further includes removing the coating. The coating is removably provided on the tooth and can be removed from the tooth at the user's discretion. For example, if a user desires to change the color of the coated tooth, and, for example, apply a different color, then the first coating is removed to expose the original tooth surfaces again. A second or next coating can then be applied to the tooth to change the color. Removing preferably includes the step of using a dental pick, or tool provided by the method, to remove the shell from the tooth.

Alternately, a solvent may be used to remove the tooth coating. Preferably, the solvent comprises a composition which the user can readily obtain, or which can be supplied to the individual, non-medical personnel user. Furthermore, it is conceivable that compatible solvents can be used for removing the covering compound from a tooth by softening or dissolving the compound or its bonds. The solvent, for example, can be a material which invades the bond formed between the compound and the tooth surface to loosen the covering compound. The removal step wherein a solvent is used, can be accomplished by swabbing the solvent onto the tooth coating or around the edges thereof with a cotton swab. The coating is then loosened and can be more easily removed.

Removal of the covering coating from the tooth then displays the original surface of the underlying tooth which had been covered by the coating.

The following are examples of the method of the present invention, as carried out on human teeth in vivo.

EXAMPLE 1

An anterior tooth was prepared by retracting the individual's lip to expose the entire tooth, up to and including the upper gum line. The tooth was a front upper tooth. The covering compound was prepared by admixing a Bis-GMA sealant with an associated catalyst. The covering compound applied was a liquid Bis-GMA sealant comprising bisphenol diglycidylmethacrylate, with small amounts (less than 7%) of silica, titanium dioxide and benzoyl peroxide. The benzoyl peroxide was added to the other components immediately prior to use. The tooth was prepared by first applying a preparatory liquid solution of 15 to 40% hydroxymethyl methacrylate in ethanol. After the preparatory liquid was brushed onto the tooth surface, the covering compound was then brushed onto the saliva-moist tooth with a small sable brush. The brushed-on covering compound was then dried naturally by exposure to air for approximately 2 minutes. The result was an evenly-coated tooth, which presented an evenly-colored appearance. Any discoloration or uneven shading which was previously present on the tooth was no longer visible.

The tooth was used normally, for eating, drinking, and was brushed regularly for a two week period, after which the coating on the tooth was easily removed by a pick. The coating was detached from the tooth and removed in one-piece as a shell.

EXAMPLE 2

The above conditions were repeated, as reported for Example 1, above, for an anterior front tooth. However, the tooth was first prepared by exposing the tooth to citric acid (applied in the form of lemon juice). The lemon juice was permitted to remain on the tooth for one minute, after which time, it was washed off of the tooth with a water rinse. The compound was then prepared and applied to the washed tooth, which was still wet, in accordance with the same procedure as in Example 1, above. This coating performed, and could be removed, in the same manner as the coating in Example 1, above.

EXAMPLE 3

An anterior tooth was prepared by retracting the individual's lip to expose the entire tooth, up to and including the upper gum line. The tooth was a front upper tooth. The covering compound was prepared by admixing a Bis-GMA sealant with an associated catalyst. The covering compound applied was a liquid Bis-GMA sealant comprising bisphenol diglycidylmethacrylate, with small amounts (less than 7%) of silica, titanium dioxide and benzoyl peroxide. The benzoyl peroxide was added to the other components immediately prior to use. A modified food starch with a titanium dioxide red #40 color additive was added to the mixture to form the covering compound. The covering compound exhibited a pinkish color. The tooth was unprepared and the colorized covering compound was then brushed onto the saliva-moist tooth with a small sable brush. The brushed-on covering compound was then dried naturally by exposure to air for approximately 2 minutes. The result was an evenly coated tooth, which exhibited a pink appearance.

The covering compound was permitted to remain on the tooth for approximately two days after which it was removed with a pick. The pick was brought into engagement with the coating on the tooth and was then pulled to remove the coating from the tooth, restoring the tooth to its original color prior to the application of the pink coating.

ADDITIONAL PROPOSED EXAMPLES

EXAMPLE 4

The covering compound is initially prepared using a glass ionomeric cement material containing a setting reactant and a binder. The covering compound is then further prepared by mixing a colorizing pigment. The colorizing pigment can be selected from color additives, including titanium dioxide and other pigments, vegetable dyes and the like. In this manner a tooth-colored shade is approximated with the addition of a pigment and by providing finely pulverized fluoroaluminosilicate glass. The covering compound is provided in a tooth color shade to the user.

The provided covering compound is then admixed with a selected pigment to provide a colorized compound. The colorized compound is applied to a saliva-most tooth by painting it on the tooth surface. The compound is then permitted to dry by exposure to air.

The coating can be removed from a tooth by scraping with a pick or can be wet with a solvent which disturbs the bond between the tooth surface and the coating. For example, removal of the coating is accomplished by absorbing the solvent onto a cotton swab and swabbing the solvent on and around the edges of the coating. The coating is therefore removed from the tooth and the original surface of the tooth exposed.

EXAMPLE 5

The covering compound is initially prepared using a glass ionomeric cement material containing a setting reactant and a binder. The covering compound is then further prepared by mixing a colorizing pigment. The colorizing pigment is selected from the pigments of the palette means. The palette means includes pigments comprising color additives, such as for example, titanium dioxide and other pigments, including vegetable dyes or food grade dyes. A containing means is used having pigment holding means for holding an array of pigments for selection by the user. The containing means also can have a mixing area wherein the selected pigments can be mixed with the glass ionomeric cement. The covering compound is prepared by selecting from the palette means one or more pigment compound selections and mixing the selected pigment compound or compounds with the glass ionomeric cement. The glass ionomeric cement can be provided in a tooth colored shade which can be further customized by the user with a selection from the pigment compounds.

The colorized compound is applied to a saliva-most tooth by painting it on the tooth surface. The compound is then permitted to dry by exposure to air.

The coating can be removed from a tooth by scraping with a pick or can be wet with a solvent which disturbs the bond between the tooth surface and the coating.

EXAMPLE 6

The methods described in Examples 3, 4, 5 and 6 above, but further including an etching step. A weak acid is provided to etch very small microscopic pits onto the tooth surface. A citric acid solution is used. The citric acid solution preferably has the same concentration as lemon juice and, further, can be used in the form of lemon juice. The lemon juice is applied onto the tooth surface which is to receive the covering compound and allowed to remain on the tooth from about a few seconds to a few minutes. The lemon juice is then washed from the tooth with a water rinse. The tooth, still wet, is now ready to receive the covering compound. The covering compound is then applied by brushing onto the tooth surface to provide an evenly dispersed coating on the tooth. The tooth is then dried.

EXAMPLE 7

The method is carried out as in Example 6, wherein the tooth preparing step includes etching the tooth with a polyacrylic acid solution by contacting the tooth with the acid solution and allowing the acid solution to remain on the tooth for a couple of minutes. The acid is then rinsed off of the tooth by applying a water rinse. Thereafter, the covering compound is applied.

EXAMPLE 8

The method is carried out as in any of examples 3, 4, 5, 6 and 7 above, wherein the glass ionomeric material is provided having a powdered component and a liquid component. The powdered component can contain the pigment, which can be a tooth colored pigment or a non-tooth colored pigment. The powdered component can be provided in a plurality of pigmented shades for selection by the user. The powdered component is selected and mixed with a liquid component to form the glass ionomeric covering material for application to an etched or non-etched tooth.

EXAMPLE 9

The method is carried out as in any of examples 3, 4, 5, 6, 7 and 8 above, wherein the glass ionomeric material includes a photoactivated curable polymerization compound. In this example, the drying step includes exposure of the covering compound to light after it is applied to the tooth in order to cure the compound. The lightsource used can, for example, comprise an ordinary house light.

EXAMPLE 10

The method is carried out as in any of examples 1 and 2 above, wherein the Bis-GMA sealant material includes a photoactivated curable polymerization compound. The drying step includes exposure of the covering compound to light after it is applied to the tooth in order to cure the compound. The lightsource used can, for example, comprise an ordinary house light.

It will be apparent to those skilled in the art that various modifications can be made to the present invention without departing from the spirit and scope of the invention, and it is intended that the present invention cover modifications and variations which are within the scope of the appended claims and their equivalents.

What is claimed is:

1. A method for cosmetically altering the appearance of teeth to whiten or colorize the teeth, comprising the steps of:
   a) preparing the tooth by exposing the tooth so that the tooth surface to be altered is visible to the gum line;
   b) preparing a removable covering compound to be removably applied onto the enamel of the tooth to be altered, including selecting a compound from a plurality of tooth colored compounds to match the shade of the adjacent or surrounding teeth in the individual's mouth;
   c) applying the removal covering compound prepared in step b. to the tooth surface to be coated;
   d) allowing the removable covering compound applied to the tooth to dry by exposing the tooth to air to expose the tooth surface on which the covering compound was applied; and
   e) selectively removing the covering compound applied to the tooth in step d. from the tooth.

2. A method for cosmetically altering the appearance of teeth to whiten or colorize the teeth, comprising the steps of:
   a) preparing the tooth by exposing the tooth so that the tooth surface to be altered is visible to the gum line;
   b) preparing a covering compound to be applied onto the enamel surface of the tooth to be altered, including selecting a compound from a plurality of tooth colored compounds to match the shade of the adjacent or surrounding teeth in the individual's mouth;
   c) applying the covering compound prepared in step b. to the tooth surface to be coated;
   d) allowing the covering compound applied to the tooth to dry by exposing the tooth to air;
   e) selectively removing the compound applied to the tooth, wherein the removal of said compound includes removing a shell comprising the compound which was applied to the tooth.

3. The method of claim 2, wherein the step of preparing a compound includes selecting a color from one or more non-tooth colored compounds and mixing said non-tooth-colored compound with said compound to provide an overall non-tooth colored appearance.

4. The method of claim 3, further including the step of providing palette means, said palette means including a plurality of pigmented compounds, and selecting one or more of said pigmented compounds from said palette means and mixing said selected one or more pigmented compounds with said the compound of step b) before applying said covering compound to said tooth.

5. The method of claim 3, further including the step of providing a food grade dye as the colorizing compound and blending said food grade dye with said covering compound.

6. The method of claim 2, wherein colorizing means is provided containing a plurality of pigments, and wherein the method further includes the steps of selecting from colorizing means at least one pigment from palette means, and mixing said selected pigment with said compound to be applied to the tooth.

7. The method of claim 6, further including the step of mixing a reflecting material into said compound to be applied to said tooth.

8. The method of claim 2, wherein the step of preparing a compound includes providing a Bis-GMA compound of the type used for filling fissures in posterior teeth.

9. The method of claim 2, wherein the step of preparing a compound includes providing glass ionomeric compound of the type used for a dental cement which can cure in the presence of saliva.

10. The method of claim 9, wherein the glass ionomeric compound provided contains pulverized fluoroaluminosilicate glass particles.

11. The method of claim 9, wherein the glass ionomeric compound contains components which are compatible in relation to the refractive index of the applied glass ionomeric compound to provide a lustrous appearance.

12. The method of claim 2, wherein the step of preparing a compound includes providing a finely divided particulate matter comprising a fluoroaluminosilicate compound and providing a liquid polymer compound in a polymerizable form, and mixing said particulate matter and liquid polymer compound.

13. The method of claim 12, wherein the pigment compound is applied to the tooth to evenly colorize the tooth by providing a pigment compound in the finely divided particulate matter which comprises the covering compound which is applied to the tooth.

14. The method of claim 2, wherein the step of preparing a covering compound further includes selecting a food grade dye and blending said dye with said covering compound to provide a colored covering on said tooth.

15. The method of claim 2, wherein the step of preparing a covering compound further comprises providing a compound in a fluidic suspension for delivery by spraying, and wherein the step of applying the covering compound to the tooth surface further comprises the step of spraying the covering compound on the tooth surface.

16. The method of claim 2, wherein the step of preparing a compound includes selecting a color from one or more non-tooth colored compounds and mixing said non-tooth-colored compound with said compound to provide an overall non-tooth colored appearance.

17. The method of claim 16, further including the step of providing palette means, said palette means including a plurality of pigmented compounds, and selecting one or more of said pigmented compounds from said palette means and mixing said selected one or more pigmented compounds with said the compound of step.

18. The method of claim 16, further including the step of providing a food grade dye as the colorizing compound and blending said food grade dye with said covering compound.

19. A method for cosmetically altering the appearance of teeth to whiten or colorize the teeth, comprising the steps of:
   a) preparing the tooth by exposing the tooth so that the tooth surface to be altered is visible to the gum line;
   b) preparing a covering compound to be applied onto the enamel surface of the tooth to be altered, including selecting a compound from a plurality of tooth colored compounds to match the shade of the adjacent or surrounding teeth in the individual's mouth;
   c) applying the covering compound prepared in step b. to the tooth surface to be coated;
   d) allowing the covering compound applied to the tooth to dry by exposing the tooth to air;

e) wherein the step of preparing a tooth further includes the step of etching microscopic pits which are less than about 5.0 μm in the tooth surface with an etchant comprising lemon juice.

20. The method of claim 19, wherein colorizing means is provided containing a plurality of pigments, and wherein the method further includes the steps of selecting from colorizing means at least one pigment from palette means, and mixing said selected pigment with said compound to be applied to the tooth.

21. The method of claim 20, further including the step of mixing a reflecting material into said compound to be applied to said tooth.

22. The method of claim 19, wherein the step of preparing a compound includes providing a Bis-GMA compound of the type used for filling fissures in posterior teeth.

23. The method of claim 19, wherein the step of preparing a compound includes providing glass ionomeric compound of the type used for a dental cement which can cure in the presence of saliva.

24. The method of claim 19, wherein the step of preparing a compound includes providing a finely divided particulate matter comprising a fluoroaluminosilicate compound and providing a liquid polymer compound in a polymerizable form, and mixing said particulate matter and liquid polymer compound.

25. The method of claim 24, wherein the glass ionomeric compound provided contains pulverized fluoroaluminosilicate glass particles.

26. The method of claim 24, wherein the glass ionomeric compound contains components which are compatible in relation to the refractive index of the applied glass ionomeric compound to provide a lustrous appearance.

27. The method of claim 19, wherein the step of preparing a covering compound further includes selecting a food grade dye and blending said dye with said covering compound to provide a colored covering on said tooth.

28. The method of claim 27, wherein the pigment compound is applied to the tooth to evenly colorize the tooth by providing a pigment compound in the finely divided particulate matter which comprises the covering compound which is applied to the tooth.

29. The method of claim 19, wherein the step of preparing a covering compound further comprises providing a compound in a fluidic suspension for delivery by spraying, and wherein the step of applying the covering compound to the tooth surface further comprises the step of spraying the covering compound on the tooth surface.

* * * * *